(12) United States Patent
Acevedo-Duncan et al.

(10) Patent No.: US 9,351,981 B2
(45) Date of Patent: May 31, 2016

(54) USE OF PKC-IOTA INHIBITORS FOR THE TREATMENT OF BREAST CANCER

(75) Inventors: Mildred Enid Acevedo-Duncan, Plant City, FL (US); Diondra Denise Hill, Tampa, FL (US); David A. Ostrov, Gainesville, FL (US)

(73) Assignees: UNIVERSITY OF SOUTH FLORIDA, Tampa, FL (US); THE UNITED STATES OF AMERICA AS REPRESENTED BY THE DEPARTMENT OF VETERANS AFFAIRS, Washington, DC (US)

( * ) Notice: Subject to any disclaimer, the term of this patent is extended or adjusted under 35 U.S.C. 154(b) by 0 days.

(21) Appl. No.: 13/821,725

(22) PCT Filed: Sep. 19, 2011

(86) PCT No.: PCT/US2011/052147
§ 371 (c)(1),
(2), (4) Date: Apr. 12, 2013

(87) PCT Pub. No.: WO2012/037553
PCT Pub. Date: Mar. 22, 2012

(65) Prior Publication Data
US 2013/0189257 A1   Jul. 25, 2013
US 2016/0106767 A9   Apr. 21, 2016

Related U.S. Application Data

(63) Continuation-in-part of application No. 12/210,576, filed on Sep. 15, 2008, now Pat. No. 8,461,192.

(60) Provisional application No. 61/384,023, filed on Sep. 17, 2010, provisional application No. 60/993,814, filed on Sep. 13, 2007.

(51) Int. Cl.
*A61K 31/66* (2006.01)
*A61K 31/675* (2006.01)
*A61K 31/4164* (2006.01)
*A61K 31/7088* (2006.01)
*A61K 39/395* (2006.01)
*C12N 15/113* (2010.01)

(52) U.S. Cl.
CPC ........... *A61K 31/675* (2013.01); *A61K 31/4164* (2013.01); *A61K 31/66* (2013.01); *A61K 31/7088* (2013.01); *A61K 39/39558* (2013.01); *C12N 15/1137* (2013.01); *C12Y 207/11013* (2013.01); *C12N 2310/14* (2013.01)

(58) Field of Classification Search
CPC . A61K 31/66; A61K 31/675; A61K 31/4164; A61K 31/7088; A61K 39/39558; C12N 15/1137; C12N 2310/14; C12Y 207/11013
See application file for complete search history.

(56) References Cited

U.S. PATENT DOCUMENTS

2003/0157082 A1 *   8/2003   Hunter et al. ................ 424/94.1

FOREIGN PATENT DOCUMENTS

WO   WO 2009036414 A1 *   3/2009

OTHER PUBLICATIONS

Schmitt et. al., Nucleosides and Nucleotides, 1995, M. Dekkar, vol. 14(9 and 10), pp. 1929-1945.*

* cited by examiner

*Primary Examiner* — Sarah Pihonak
(74) *Attorney, Agent, or Firm* — Saliwanchik, Lloyd & Eisenschenk

(57) ABSTRACT

The subject invention pertains to uses of PKC-iota inhibitors for treatment of breast cancer. In one embodiment, the subject invention provides novel uses of 1H-imidazole-4-carboxamide, 5-amino-1-[2,3-dihydroxy-4-[(phosphonooxy)methyl] cyclopentyl]-,[1R-(1α, 2β, 3β, 4α)] (ICA-1) and related compounds for treatment of breast cancer. The compounds of the subject invention have potent anti-proliferative effects against human breast cancer cells. The compounds of the subject invention also inhibit the phosphorylation of IKK-α/IKK-β, induce chromatin condensation, and/or induce DNA fragmentation in cancer cells.

8 Claims, 4 Drawing Sheets

SEQUENCE LISTING

<160> NUMBER OF SEQ ID NOS: 7

<210> SEQ ID NO 1
<211> LENGTH: 587
<212> TYPE: PRT
<213> ORGANISM: Homo sapiens

<400> SEQUENCE: 1

```
Met Ser His Thr Val Ala Gly Gly Ser Gly Asp His Ser His Gln
1               5                   10                  15

Val Arg Val Lys Ala Tyr Tyr Arg Gly Asp Ile Met Ile Thr His Phe
                20                  25                  30

Glu Pro Ser Ile Ser Phe Glu Gly Leu Cys Asn Glu Val Arg Asp Met
                35                  40                  45

Cys Ser Phe Asp Asn Glu Gln Leu Phe Thr Met Lys Trp Ile Asp Glu
        50                  55                  60

Glu Gly Asp Pro Cys Thr Val Ser Ser Gln Leu Glu Leu Glu Glu Ala
65                  70                  75                  80

Phe Arg Leu Tyr Glu Leu Asn Lys Asp Ser Glu Leu Leu Ile His Val
                85                  90                  95

Phe Pro Cys Val Pro Glu Arg Pro Gly Met Pro Cys Pro Gly Glu Asp
                100                 105                 110

Lys Ser Ile Tyr Arg Arg Gly Ala Arg Arg Trp Arg Lys Leu Tyr Cys
            115                 120                 125

Ala Asn Gly His Thr Phe Gln Ala Lys Arg Phe Asn Arg Arg Ala His
        130                 135                 140

Cys Ala Ile Cys Thr Asp Arg Ile Trp Gly Leu Gly Arg Gln Gly Tyr
145                 150                 155                 160

Lys Cys Ile Asn Cys Lys Leu Leu Val His Lys Lys Cys His Lys Leu
                165                 170                 175

Val Thr Ile Glu Cys Gly Arg His Ser Leu Pro Gln Glu Pro Val Met
                180                 185                 190

Pro Met Asp Gln Ser Ser Met His Ser Asp His Ala Gln Thr Val Ile
            195                 200                 205

Pro Tyr Asn Pro Ser Ser His Glu Ser Leu Asp Gln Val Gly Glu Glu
        210                 215                 220

Lys Glu Ala Met Asn Thr Arg Glu Ser Gly Lys Ala Ser Ser Ser Leu
225                 230                 235                 240

Gly Leu Gln Asp Phe Asp Leu Leu Arg Val Ile Gly Arg Gly Ser Tyr
                245                 250                 255

Ala Lys Val Leu Leu Val Arg Leu Lys Lys Thr Asp Arg Ile Tyr Ala
                260                 265                 270

Met Lys Val Val Lys Lys Glu Leu Val Asn Asp Asp Glu Asp Ile Asp
            275                 280                 285

Trp Val Gln Thr Glu Lys His Val Phe Glu Gln Ala Ser Asn His Pro
        290                 295                 300

Phe Leu Val Gly Leu His Ser Cys Phe Gln Thr Glu Ser Arg Leu Phe
305                 310                 315                 320

Phe Val Ile Glu Tyr Val Asn Gly Gly Asp Leu Met Phe His Met Gln
                325                 330                 335

Arg Gln Arg Lys Leu Pro Glu Glu His Ala Arg Phe Tyr Ser Ala Glu
```

```
                340             345                 350
Ile Ser Leu Ala Leu Asn Tyr Leu His Glu Arg Gly Ile Ile Tyr Arg
            355                 360                 365
Asp Leu Lys Leu Asp Asn Val Leu Leu Asp Ser Glu Gly His Ile Lys
            370                 375             380
Leu Thr Asp Tyr Gly Met Cys Lys Glu Gly Leu Arg Pro Gly Asp Thr
385                 390                 395                 400
Thr Ser Thr Phe Cys Gly Thr Pro Asn Tyr Ile Ala Pro Glu Ile Leu
                405                 410                 415
Arg Gly Glu Asp Tyr Gly Phe Ser Val Asp Trp Trp Ala Leu Gly Val
            420                 425             430
Leu Met Phe Glu Met Met Ala Gly Arg Ser Pro Phe Asp Ile Val Gly
            435                 440             445
Ser Ser Asp Asn Pro Asp Gln Asn Thr Glu Asp Tyr Leu Phe Gln Val
            450                 455             460
Ile Leu Glu Lys Gln Ile Arg Ile Pro Arg Ser Leu Ser Val Lys Ala
465             470                 475             480
Ala Ser Val Leu Lys Ser Phe Leu Asn Lys Asp Pro Lys Glu Arg Leu
                485                 490             495
Gly Cys His Pro Gln Thr Gly Phe Ala Asp Ile Gln Gly His Pro Phe
            500                 505             510
Phe Arg Asn Val Asp Trp Asp Met Met Glu Gln Lys Gln Val Val Pro
            515                 520             525
Pro Phe Lys Pro Asn Ile Ser Gly Glu Phe Gly Leu Asp Asn Phe Asp
            530                 535             540
Ser Gln Phe Thr Asn Glu Pro Val Gln Leu Thr Pro Asp Asp Asp Asp
545             550                 555             560
Ile Val Arg Lys Ile Asp Gln Ser Glu Phe Glu Gly Phe Glu Tyr Ile
                565                 570             575
Asn Pro Leu Leu Met Ser Ala Glu Glu Cys Val
            580             585

<210> SEQ ID NO 2
<211> LENGTH: 19
<212> TYPE: DNA
<213> ORGANISM: Artificial Sequence
<220> FEATURE:
<223> OTHER INFORMATION: single strand of PKC-iota siRNA

<400> SEQUENCE: 2
caagccaagc guucaaca                                                19

<210> SEQ ID NO 3
<211> LENGTH: 19
<212> TYPE: DNA
<213> ORGANISM: Artificial Sequence
<220> FEATURE:
<223> OTHER INFORMATION: a single strand of PKC-iota siRNA

<400> SEQUENCE: 3
uguugaaacg cuuggcuug                                               19

<210> SEQ ID NO 4
<211> LENGTH: 19
<212> TYPE: DNA
<213> ORGANISM: Artificial Sequence
<220> FEATURE:
<223> OTHER INFORMATION: a single strand of PKC-iota siRNA
```

```
<400> SEQUENCE: 4
ggaacgauug gguugucau                                                        19

<210> SEQ ID NO 5
<211> LENGTH: 20
<212> TYPE: DNA
<213> ORGANISM: Artificial Sequence
<220> FEATURE:
<223> OTHER INFORMATION: a single strand of PKC-iota siRNA

<400> SEQUENCE: 5
augacaaccc aaucguuucc                                                       20

<210> SEQ ID NO 6
<211> LENGTH: 19
<212> TYPE: DNA
<213> ORGANISM: Artificial Sequence
<220> FEATURE:
<223> OTHER INFORMATION: a single strand of PKC-iota siRNA

<400> SEQUENCE: 6
cccaauaucu ucucuugua                                                        19

<210> SEQ ID NO 7
<211> LENGTH: 19
<212> TYPE: DNA
<213> ORGANISM: Artificial Sequence
<220> FEATURE:
<223> OTHER INFORMATION: a single strand of PKC-iota siRNA

<400> SEQUENCE: 7
uacaagagaa gauauuggg                                                        19
```

USE OF PKC-IOTA INHIBITORS FOR THE TREATMENT OF BREAST CANCER

CROSS-REFERENCE TO RELATED APPLICATION

This application is the U.S. national stage application of International Patent Application No. PCT/US2011/052147, filed Sep. 19, 2011, which claims the benefit of U.S. Provisional Patent Application No. 61/384,023, filed Sep. 17, 2010, the disclosures of each of which are hereby incorporated by reference in their entirety. This application is a continuation-in-part of U.S. patent application Ser. No. 12/210,576, filed Sep. 15, 2008, now U.S. Pat. No. 8,461,192, issued Jun. 11, 2013; which claims the benefit of U.S. Provisional Patent Application No. 60/993,814, filed Sep. 13, 2007.

BACKGROUND OF THE INVENTION

Breast cancer is the most common female malignancy and the leading cause of cancer-related death among women. The 2009 cancer statistics estimated that 181,000 new cases of invasive breast cancer were diagnosed that year and would result in 46,300 new deaths. In North America, breast cancer accounts for about 27% of all female cancers and 15%-20% of all female cancer mortalities. While advancement in the diagnosis and treatment of breast cancer has prolonged patient survival, alternative therapeutic agents for treatment of breast cancer are needed.

Protein kinase C-iota (PKC-ι), an atypical protein kinase C isozyme, plays an essential role in the growth, proliferation and survival of many types of cancer cells. PKC-ι has been shown to promote cell survival in ovarian cancer, non-small cell lung cancer and prostate cancer. However, PKC-ι has not previously been reported to play any role in breast cancer. It also remains unknown whether agents that inhibit PKC-ι activity would have any effect on the treatment of breast cancer.

BRIEF SUMMARY OF THE INVENTION

The subject invention provides use of PKC-iota (PKC-ι) inhibitors for treatment of breast cancer. PKC-ι inhibitors useful according to the subject invention include, but are not limited to, agents that inhibit PKC-ι activity; and agents that reduce or inhibit the expression of PKC-iota.

In certain embodiments, the subject invention can be used to treat or ameliorate breast cancer including, but not limited to, ductal carcinoma in-situ (DCIS), invasive ductal carcinoma (IDC), lobular carcinoma in-situ (LCIS), invasive lobular carcinoma (LCIS), medullary carcinoma, malignant phyllode tumor, tubular carcinoma, mucinous carcinoma, metastatic adenocarcinoma, and inflammatory breast cancer.

In one embodiment, the subject invention pertains to novel uses of 1H-imidazole-4-carboxamide, 5-amino-1-[2,3-dihydroxy-4-[(phosphonooxy)methyl]cyclopentyl]-[1R-(1α, 2β, 3β, 4α)] (ICA-1) and related compounds for treatment of breast cancer. Surprisingly, the compounds of the subject invention have potent anti-proliferative effects against human breast cancer cells. The compounds of the subject invention also inhibit the phosphorylation of IKK-α/IKK-β, induce chromatin condensation, and/or induce DNA fragmentation in cancer cells.

In an embodiment, the subject invention provides a method for treating breast cancer, comprising administering to a subject in need of such treatment an effective amount of a compound of Formula I:

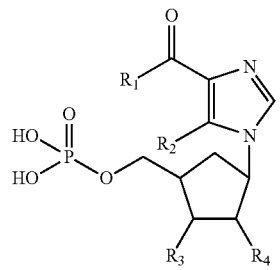

wherein $R_1$ and $R_2$ are, independently, —$NH_2$ or alkylamino, and wherein $R_3$ and $R_4$ are, independently, —H, —OH, alkoxy, or —OC(O)R', wherein R' is a linear saturated monovalent radical of one to eight carbon atoms or a branched saturated monovalent of three to eight carbon atoms.

In an embodiment, the subject invention further comprises administering to the subject a second therapeutic agent including, but not limited to, taxanes, e.g., paclitaxel (TAXOL, BRISTOL-MYERS SQUIBB Oncology, Princeton, N.J.) and doxetaxel (TAXOTERE, Rhone-Poulenc Rorer, Antony, France), chlorambucil, vincristine, vinblastine, gemcitabine, ixabepilone, doxorubicin, anti-estrogens such as tamoxifen and raloxifene, aromatase inhibitors such as 4(5)-imidazoles, 4-hydroxytamoxifen, trioxifene, keoxifene, LY117018, onapristone, and toremifene (Fareston), and anti-androgens such as flutamide, nilutamide, bicalutamide, leuprolide, and goserelin, and immuno-modulating agents.

BRIEF DESCRIPTION OF THE SEQUENCES

SEQ ID NO: 1 is an amino acid sequence of human Protein kinase C-iota (PKC-ι).

SEQ ID NO: 2 5'-CAAGCCAAGCGUUUCAACA-3' is a single strand of PKC-ι siRNA.

SEQ ID NO: 3 5'-UGUUGAAACGCUUGGCUUG-3' is a single strand of PKC-ι siRNA.

SEQ ID NO: 4 5'-GGAACGAUUGGGUUGUCAU-3' is a single strand of PKC-ι siRNA.

SEQ ID NO: 5 5'-AUGACAACCCAAUCGUUUCC-3' is a single strand of PKC-ι siRNA.

SEQ ID NO: 6 5'-CCCAAUAUCUUCUCUUGUA-3' is a single strand of PKC-ι siRNA.

SEQ ID NO: 7 5'-UACAAGAGAAGAUAUUGGG3' is a single strand of PKC-ι siRNA.

DETAILED DISCLOSURE OF THE INVENTION

The subject invention provides use of PKC-iota (PKC-ι) inhibitors for treatment of breast cancer. In one embodiment, the method comprises administering, to a subject in need of such treatment, an effective amount of a PKC-iota (PKC-ι) inhibitor. PKC-ι inhibitors useful according to the subject invention include, but are not limited to, agents that inhibit PKC-ι activity; and agents that reduce or inhibit the expression of PKC-iota.

In one embodiment, the subject invention pertains to therapeutic uses of (1H-imidazole-4-carboxamide,5-amino-1-[2,3-dihydroxy-4-[(phosphonooxy)ethyl]cyclopentyl], [1R-(1α, 2β, 3β, 4α)] (ICA-1) and related compounds for, in an embodiment, treatment of breast cancer. In an embodiment, the method comprises administering to a subject in need of such treatment an effective amount of ICA-1 and/or related compounds, or any salts thereof. The subject invention further provides therapeutic compositions that contain a therapeutically effective amount of the compound of the subject invention and a pharmaceutically acceptable carrier or adjuvant.

Surprisingly, it has now been discovered that (1H-imidazole-4-carboxamide,5-amino-1-[2,3-dihydroxy-4-[(phosphonooxy)methyl]cyclopentyl]-,[1R-(1α, 2β, 3β, 4α)] (ICA-1), an inhibitor of protein kinase C-iota (PKC-ι), has potent anti-proliferative effects against human breast cancer cells. MDA-MB-468 breast cancer cells were treated with 0.1 μM or 0.5 μM ICA-1, and cell viability and cell count were determined 24 hours post-treatment. ICA-1 potently decreased the proliferation of MDA-MB-468 cells by 77% (0.1 μM) and 50% (0.5 μM; P=0.05). In addition, ICA-1 inhibits the phosphorylation of IKK-α/IKK-β.

The present inventors have also discovered that ICA-1 binds to the catalytic domain of human PKC-ι (SEQ ID NO:1, GenBank Accession No. AAB17011) at amino acid residues 469-475 (glutamine-469, isoleucine-470, arginine-471, isoleucine-472, proline-473, arginine-474, serine-475). The binding of ICA-1 to PKC-ι potently inhibits the activity of PKC-ι, an oncogenic protein kinase C (PKC) isozyme that plays a critical role in the proliferation and survival of cancer cells.

In addition, the present inventors have discovered that ICA-1 promotes apoptosis of cancer cells. Specifically, ICA-1 induced chromatin condensation in cancer cells, as shown by 4',6-diamidino-2-phenylindole (DAPI) staining of the nucleus. ICA-1 also induced DNA fragmentation in cancer cells, as indicated by 3' terminal deoxynucleotidyltransferase (TdT)-mediated dUTP nick end-labeling (TUNEL) assay.

In an embodiment, the subject invention pertains to therapeutic use of 1H-imidazole-4-carboxamide,5-amino-1-[2,3-dihydroxy-4-[(phosphonooxy)methyl]cyclopentyl]-,[1R-(1α, 2β, 3β, 4α)] (ICA-1), having the following structure:

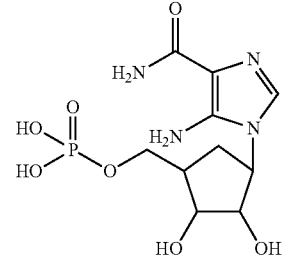 [SMILES: NC(=O)c1ncn(C2CC(COP(=O)(O)O)C(O)C2O)c1N]

Figure 5:
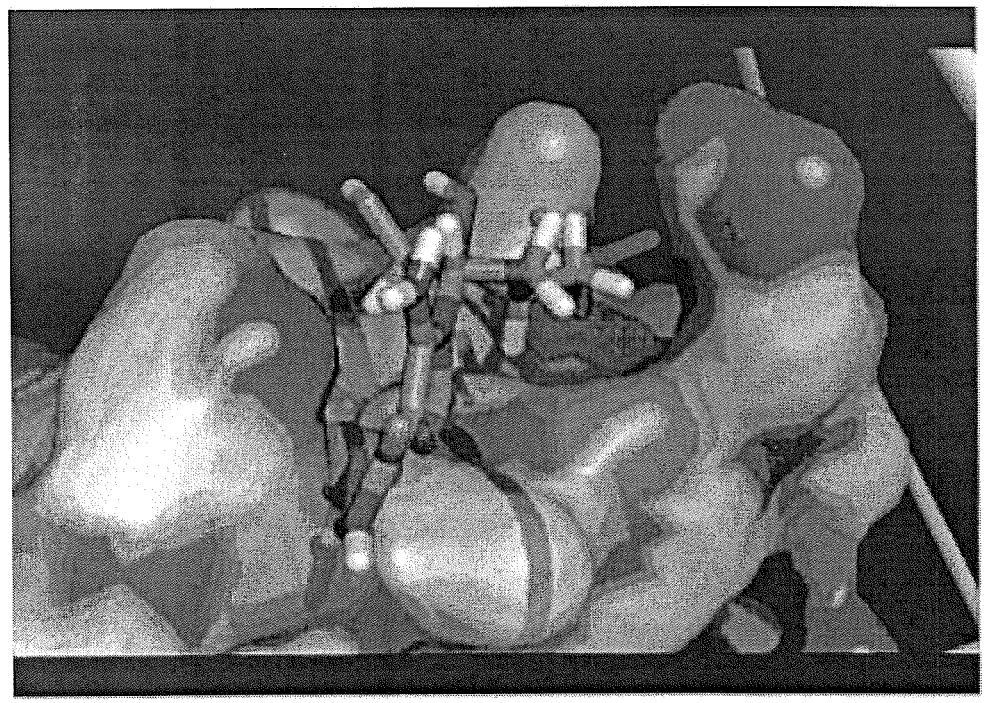
FIG. 5 displays the molecular docking of ICA-1 on amino acid residues 469-475 of the catalytic domain of PKC-ι.

Based on the molecular docking of ICA-1 on amino acid residues 469-475 of the catalytic domain of PKC-ι shown in FIG. 5, the subject invention further contemplates compounds of Formula I, which reduce or inhibit PKC-ι activity. The compounds of Formula I include ICA-1 as well as ester, ether, and alkyl substituted derivatives of ICA-1, having the following structure:

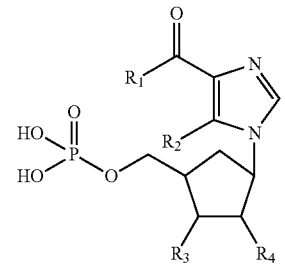

wherein $R_1$ and $R_2$ are, independently, —NH$_2$ or alkylamino, and wherein $R_3$ and $R_4$ are, independently, —H, —OH, alkoxy, or —OC(O)R', wherein R' is a linear saturated monovalent radical of one to eight carbon atoms or a branched saturated monovalent of three to eight carbon atoms.

"Alkyl" means linear saturated monovalent radicals of one to eight carbon atoms or a branched saturated monovalent of three to eight carbon atoms. It may include hydrocarbon radicals of one to four or one to three carbon atoms, which may be linear. Examples include methyl, ethyl, propyl, 2-propyl, n-butyl, iso-butyl, tert-butyl, pentyl, and the like.

"Alkylamino" means a radical —NHR or —NR$_2$ where each R is independently an alkyl group. Examples include methylamino, (1-methylethyl)amino, methylamino, dimethylamino, methylethylamino, di(1-methyethyl)amino, and the like.

"Alkoxy" means the radical —OR$_a$, where R$_a$ is an alkyl group. Exemplary alkoxy groups include methoxy, ethoxy, propoxy, and the like.

"Carboalkoxy," as used herein, refers to a radical —C(O)R where R is, for example, hydrogen, alkyl or cycloalkyl, heterocycloalkyl, or alkyl halo.

"Halo," as used herein, refers to fluoro, chloro, bromo, or iodo.

"Haloalkyl," as used herein, refers to alkyl substituted with one or more same or different halo atoms, e.g., —CH$_2$Cl, —CH$_2$Br, —CF$_3$, —CH$_2$CH$_2$Cl, —CH$_2$CCl$_3$, and the like.

The compounds of Formula I bind to PKC-ι, preferably, amino acid residues 469-475 of human PKC-ι (SEQ ID NO:1). Preferably, the compounds of Formula I also inhibit the phosphorylation of IKK-α/IKK-β. Preferably, the compounds of Formula I induce chromatin condensation in cancer cells. Preferably, the compounds of Formula I also induce DNA fragmentation in cancer cells.

The subject invention also pertains to salt forms of ICA-1 and related compounds including, but not limited to, ammonium salts, sodium salts, potassium salts, calcium salts, and magnesium salts.

PKC-ι inhibitors useful according to the subject invention also include, for example, antibodies, peptide aptamers, or binding partners that bind specifically to PKC-ι; and antisense polynucleotides (e.g., siRNAs) that target PKC-iota transcripts. The skilled artisan would readily appreciate that anti-PKC-ι antibodies or peptide aptamers can be designed to bind any PKC-ι sequences publically known, and antisense polynucleotides that target PKC-ι transcripts can be designed to target any PKC-ι mRNAs publically known.

In one embodiment, the PKC-ι inhibitor is an antibody or peptide aptamer that binds specifically to PKC-ι. In a specific embodiment, the PKC-ι inhibitor is an antibody or peptide aptamer that binds specifically to PKC-ι. In a further specific embodiment, the PKC-ι inhibitor is an antibody or peptide aptamer that binds specifically to human PKC-ι. In a further specific embodiment, the PKC-ι inhibitor is an antibody or peptide aptamer that binds specifically to a human PKC-ι of SEQ ID NO:1.

In some embodiments, the PKC-ι inhibitor is an antibody or peptide aptamer that binds specifically to a naturally-occurring or recombinant form of PKC-ι polypeptide, comprising an amino acid sequence having at least 80%, 85%, 90%, 95%, 97%, or 99% identity to SEQ ID NO:1, wherein the PKC-ι polypeptide comprises a catalytic domain that is amino acid residues 469-475 of SEQ ID NO:1 (glutamine-469, isoleucine-470, arginine-471, isoleucine-472, proline-473, arginine-474, serine-475).

Unless otherwise specified, as used herein, percent sequence identity and/or similarity of two sequences can be determined using the algorithm of Karlin and Altschul (1990), modified as in Karlin and Altschul (1993). Such an algorithm is incorporated into the NBLAST and XBLAST programs of Altschul et al. (1990). BLAST searches can be performed with the NBLAST program, score=100, wordlength=12, to obtain sequences with the desired percent sequence identity. To obtain gapped alignments for comparison purposes, Gapped BLAST can be used as described in Altschul et al. (1997). When utilizing BLAST and Gapped BLAST programs, the default parameters of the respective programs (NBLAST and XBLAST) can be used. See NCBI/NIH website.

"Specific binding" or "specificity" refers to the ability of a protein to detectably bind an epitope presented on a protein or polypeptide molecule of interest, while having relatively little detectable reactivity with other proteins or structures. Specificity can be relatively determined by binding or competitive binding assays, using, e.g., Biacore instruments. Specificity can be exhibited by, e.g., an about 10:1, about 20:1, about 50:1, about 100:1, 10.000:1 or greater ratio of affinity/avidity in binding to the specific target molecule versus nonspecific binding to other irrelevant molecules.

Anti-PKC-ι antibodies of the subject invention can be in any of a variety of forms, including intact immunoglobulin molecules, fragments of immunoglobulin molecules such as Fv, Fab and similar fragments; multimers of immunoglobulin molecules (e.g., diabodies, triabodies, and bi-specific and tri-specific antibodies, as are known in the art; see, e.g., Hudson and Kortt, J. Immunol. Methods 231:177 189, 1999); fusion constructs containing an antibody or antibody fragment; and human or humanized immunoglobulin molecules or fragments thereof.

Antibodies within the scope of the invention can be of any isotype, including IgG, IgA, IgE, IgD, and IgM. IgG isotype antibodies can be further subdivided into IgG1, IgG2, IgG3, and IgG4 subtypes. IgA antibodies can be further subdivided into IgA1 and IgA2 subtypes.

Antibodies of the subject invention include polyclonal and monoclonal antibodies. The term "monoclonal antibody," as used herein, refers to an antibody or antibody fragment obtained from a substantially homogeneous population of antibodies or antibody fragments (i.e. the individual antibodies within the population are identical except for possible naturally occurring mutations that may be present in a small subset of the antibody molecules).

A monoclonal antibody composition is typically composed of antibodies produced by clones of a single cell called a hybridoma that secretes (produces) only one type of antibody molecule. The hybridoma cell is formed by fusing an antibody-producing cell and a myeloma or other self-perpetuating cell line. Such antibodies were first described by Kohler and Milstein, *Nature*, 1975, 256:495-497, the disclosure of which is herein incorporated by reference. An exemplary hybridoma technology is described by Niman et al., *Proc. Natl. Acad. Sci. U.S.A.*, 1983, 80:4949-4953. Other methods of producing monoclonal antibodies, a hybridoma cell, or a hybridoma cell culture are also well known. See e.g., Antibodies: A Laboratory Manual, Harlow et al., Cold Spring Harbor Laboratory, 1988; or the method of isolating monoclonal antibodies from an immunological repertoise as described by Sasatry, et al., *Proc. Natl. Acad. Sci. USA*, 1989, 86:5728-5732; and Huse et al., *Science*, 1981, 246:1275-1281. The references cited are hereby incorporated herein by reference.

In one embodiment of the invention, monoclonal antibodies specific for PKC-ι can be used as a delivery vehicle for drug or toxin. Drug or toxin can be conjugated to the antibodies using a biochemical approach. Monoclonal antibodies specific for the amino-terminus of PKC-ι can be used as a delivery vehicle for drug or toxin. This enables the transport of drug or toxin to tumor cells with high expression of PKC-ι.

In some embodiments, PKC-ι inhibitors useful according to the subject invention are agents that reduce or inhibit the expression of PKC-iota, such as agents that inhibit the transcription, translation, and/or processing of PKC-iota.

In an embodiment, the PKC-ι inhibitor is a PKC-ι antisense polynucleotide. In an embodiment, the PKC-ι inhibitor is an antisense polynucleotide that targets human PKC-ι mRNA. In some embodiments, the PKC-ι antisense polynucleotides target PKC-ι mRNAs of non-human animals including, but not limited to, apes, chimpanzees, orangutans, monkeys, dogs, cats, horses, cattle, pigs, sheep, goats, chickens, mice, rats, and guinea pigs. The skilled artisan would readily appreciate that the antisense polynucleotides can be designed to target any PKC-ι mRNAs publically known.

In some embodiments, the PKC-ι inhibitor is a siRNA having a sequence sufficiently complementary to a target PKC-ι mRNA sequence to direct target-specific RNA interference (RNAi). In some embodiments, the PKC-ι inhibitor is siRNA having a sequence sufficiently complementary to a target human PKC-ι mRNA sequence (such as mRNA encoding SEQ ID NO:1) to direct target-specific RNA interference.

In some embodiments, the PKC-ι inhibitor is a siRNA having a sequence sufficiently complementary to a target PKC-ι mRNA sequence, wherein the target PKC-ι mRNA sequence encodes a naturally-occurring or recombinant form of a PKC-ι polypeptide comprising an amino acid sequence having at least 80%, 85%, 90%, 95%, 97%, or 99% identity to SEQ ID NO:1, wherein the PKC-ι polypeptide comprises a catalytic domain that is amino acid residues 469-475 of SEQ ID NO:1 (glutamine-469, isoleucine-470, arginine-471, isoleucine-472, proline-473, arginine-474, serine-475).

Examples of siRNA that target human PKC-ι mRNA include SEQ ID NOs: 2-7.

Examples of antisense polynucleotides include, but are not limited to, single-stranded DNAs and RNAs that bind to complementary target PKC-iota mRNA and inhibit translation and/or induce RNaseH-mediated degradation of the target transcript; siRNA oligonucleotides that target or mediate PKC-ι mRNA degradation; ribozymes that cleave PKC-ι mRNA transcripts; and nucleic acid aptamers and decoys, which are non-naturally occurring oligonucleotides that bind to and block PKC-ι protein targets in a manner analogous to small molecule drugs.

The term "nucleotide" refers to a nucleoside having one or more phosphate groups joined in ester linkages to the sugar moiety. Exemplary nucleotides include nucleoside monophosphates, diphosphates and triphosphates. The terms "polynucleotide" and "nucleic acid molecule" are used interchangeably herein and refer to a polymer of nucleotides joined together by a phosphodiester linkage between 5' and 3' carbon atoms. The terms "nucleic acid" or "nucleic acid sequence" encompass an oligonucleotide, nucleotide, polynucleotide, or a fragment of any of these, DNA or RNA of genomic or synthetic origin, which may be single-stranded or double-stranded and may represent a sense or antisense strand, peptide nucleic acid (PNA), or any DNA-like or RNA-like material, natural or synthetic in origin. As will be understood by those of skill in the art, when the nucleic acid is RNA, the deoxynucleotides A, G, C, and T are replaced by ribonucleotides A, G, C, and U, respectively.

As used herein, the term "RNA" or "RNA molecule" or "ribonucleic acid molecule" refers generally to a polymer of ribonucleotides. The term "DNA" or "DNA molecule" or "deoxyribonucleic acid molecule" refers generally to a polymer of deoxyribonucleotides. DNA and RNA molecules can be synthesized naturally (e.g., by DNA replication or transcription of DNA, respectively). RNA molecules can be post-transcriptionally modified. DNA and RNA molecules can also be chemically synthesized. DNA and RNA molecules can be single-stranded (i.e., ssRNA and ssDNA, respectively) or multi-stranded (e.g., double stranded, i.e., dsRNA and dsDNA, respectively). Based on the nature of the invention, however, the term "RNA" or "RNA molecule" or "ribonucleic acid molecule" can also refer to a polymer comprising primarily (i.e., greater than 80% or, preferably greater than 90%) ribonucleotides but optionally including at least one non-ribonucleotide molecule, for example, at least one deoxyribonucleotide and/or at least one nucleotide analog.

As used herein, the term "nucleotide analog", also referred to herein as an "altered nucleotide" or "modified nucleotide" refers to a non-standard nucleotide, including non-naturally occurring ribonucleotides or deoxyribonucleotides. Preferred nucleotide analogs are modified at any position so as to alter certain chemical properties of the nucleotide yet retain the ability of the nucleotide analog to perform its intended function.

As used herein, the term "RNA interference" ("RNAi") refers to a selective intracellular degradation of RNA. RNAi occurs in cells naturally to remove foreign RNAs (e.g., viral RNAs). Natural RNAi proceeds via fragments cleaved from free dsRNA which direct the degradative mechanism to other similar RNA sequences. Alternatively, RNAi can be initiated by the hand of man, for example, to silence the expression of endogenous target genes, such as PKC-ι.

As used herein, the term "small interfering RNA" ("siRNA") (also referred to in the art as "short interfering RNAs") refers to an RNA (or RNA analog) comprising between about 10-50 nucleotides (or nucleotide analogs) which is capable of directing or mediating RNA interference.

As used herein, a siRNA having a "sequence sufficiently complementary to a target mRNA sequence to direct target-specific RNA interference (RNAi)" means that the siRNA has a sequence sufficient to trigger the destruction of the target mRNA (e.g., PKC-ι mRNA) by the RNAi machinery or process. "mRNA" or "messenger RNA" or "transcript" is single-stranded RNA that specifies the amino acid sequence of one or more polypeptides. This information is translated during protein synthesis when ribosomes bind to the mRNA.

The subject invention also contemplates vectors (e.g., viral vectors) and expression constructs comprising the nucleic acid molecules useful for inhibiting PKC-ι expression and/or activity. In an embodiment, the vector comprises a siRNA that targets PKC-ι mRNA. In another embodiment, the vector comprises a nucleic acid molecule encoding an anti-PKC-ι antibody.

As used herein, the term "expression construct" refers to a combination of nucleic acid sequences that provides for transcription of an operably linked nucleic acid sequence. As used herein, the term "operably linked" refers to a juxtaposition of the components described, wherein the components are in a relationship that permits them to function in their intended manner. In general, operably linked components are in contiguous relation.

Expression constructs of the invention will also generally include regulatory elements that are functional in the intended host cell in which the expression construct is to be expressed. Thus, a person of ordinary skill in the art can select regulatory elements for use in, for example, bacterial host cells, yeast host cells, mammalian host cells, and human host cells. Regulatory elements include promoters, transcription termination sequences, translation termination sequences, enhancers, and polyadenylation elements.

An expression construct of the invention can comprise a promoter sequence operably linked to a polynucleotide sequence encoding a peptide of the invention. Promoters can be incorporated into a polynucleotide using standard techniques known in the art. Multiple copies of promoters or multiple promoters can be used in an expression construct of the invention. In a preferred embodiment, a promoter can be positioned about the same distance from the transcription start site as it is from the transcription start site in its natural genetic environment. Some variation in this distance is permitted without substantial decrease in promoter activity. A transcription start site is typically included in the expression construct.

In a further embodiment, the subject invention provides a method of inhibiting proliferation of breast cancer or tumor cells, comprising administering to the breast cancer or tumor cells an effective amount of a PKC-iota inhibitor, and optionally, a pharmaceutically acceptable carrier.

Treatment of Breast Cancer

The subject invention provides use of PKC-iota (PKC-ι) inhibitors for treatment of breast cancer. In a specific embodiment, the subject invention provides a method for treatment of breast cancer via the administration of ICA-1 and related compounds to a subject. The method comprises administering to a subject in need of such treatment an effective amount of a compound of Formula I (e.g., ICA-1) or salt thereof.

The term "treatment" or any grammatical variation thereof (e.g., treat, treating, and treatment etc.), as used herein, includes but is not limited to, ameliorating or alleviating a symptom of a disease or condition, reducing, suppressing, inhibiting, lessening, or affecting the progression and/or severity of an undesired physiological change or a diseased condition. For instance, treatment includes, for example, slowing the growth and/or proliferation of breast cancer cells; reducing breast tumor size; reducing the number of breast cancer cells; inhibiting or slowing the invasion of breast cancer cells into surrounding or neighboring tissues; inhibiting or slowing the metastatic spread of breast cancer cells into distant parts of the body; alleviating symptoms associated with breast cancer; and prolonging breast cancer patient survival.

The term "effective amount," as used herein, refers to an amount that is capable of treating or ameliorating a disease or condition or otherwise capable of producing an intended therapeutic effect. In certain embodiments, the effective amount enables a 5%, 10%, 20%, 30%, 40%, 50%, 75%, 90%, 95%, 99% or 100% reduction in the rate of breast cancer growth and/or proliferation. In certain embodiments, the effective amount enables a 5%, 10%, 15%, 20%, 25%, 30%, 35% or 40% reduction in breast tumor size.

The term "subject," as used herein, describes an organism, including mammals such as primates, to which treatment with the compositions according to the subject invention can be administered. Mammalian species that can benefit from the disclosed methods include, but are not limited to, apes, chimpanzees, orangutans, humans, monkeys; and other animals such as dogs, cats, horses, cattle, pigs, sheep, goats, chickens, mice, rats, guinea pigs, and hamsters. Typically, the subject is a human.

In an embodiment, subjects in need of such treatment are diagnosed with breast cancer or tumor. By way of example, breast tumor can be identified by routine diagnostic or screening techniques such as X rays (e.g., mammography), ultrasound, magnetic resonance imaging (MRI), needle biopsies, stereotactic breast biopsies, MRI-guided breast biopsies, and surgical biopsies. Molecular and phenotypic analysis of cancer cells within a tissue will usually confirm if the cancer is endogenous to the breast tissue or if the lesion is due to metastasis from another site.

In an embodiment, the subject invention provides a method for treating or ameliorating breast cancer. In an embodiment, the compounds of the subject invention can be used to treat or ameliorate primary breast cancer, in which cancer cells originated from breast tissue have not spread past the breast to distant parts of the body. In a specific embodiment, the compounds of the subject invention can be used to treat or ameliorate non-invasive and/or invasive breast cancer.

In certain embodiments, the subject invention can be used to treat or ameliorate breast cancer, including ductal carcinoma in-situ (DCIS), invasive ductal carcinoma (IDC), lobular carcinoma in-situ (LCIS), invasive lobular carcinoma (LCIS), medullary carcinoma, malignant phyllode tumor, tubular carcinoma, mucinous carcinoma, metastatic adenocarcinoma, and inflammatory breast cancer. In preferred embodiments, the subject invention can be used to treat or ameliorate invasive ductal carcinoma and/or invasive lobular carcinoma.

In another embodiment, the subject invention can be used to treat or ameliorate metastatic breast cancer, in which cancer cells originated from breast tissue have spread past the breast to distant parts of the body such as the bones, lungs, and liver. In anther embodiment, the subject invention can be used to treat or ameliorate recurrent breast cancer.

While benign breast tumors normally do not increase the risk of breast cancer and thus are often left untreated, the subject invention can be used to treat or ameliorate benign breast tumors such as fibroadenoma.

In a further embodiment, the compounds of the subject invention can be used in combination with another anti-cancer therapy including, but not limited to, surgery, radiation therapy, chemotherapy, DNA therapy, adjuvant therapy, and gene therapy. In a specific embodiment, the subject invention comprises administering to the subject a second therapeutic agent. The second therapeutic agent can be administered before, during or after the administration of the compound of Formula I.

Second therapeutic agents for treatment of breast cancer include, but are not limited to, taxanes, e.g., paclitaxel (TAXOL, BRISTOL-MYERS SQUIBB Oncology, Princeton, N.J.) and doxetaxel (TAXOTERE, Rhone-Poulenc Rorer, Antony, France), chlorambucil, vincristine, vinblastine, gemcitabine, ixabepilone, doxorubicin, anti-estrogens such as tamoxifen and raloxifene, aromatase inhibitors such as 4(5)-imidazoles, 4-hydroxytamoxifen, trioxifene, keoxifene, LY117018, onapristone, and toremifene (Fareston), and anti-androgens such as flutamide, nilutamide, bicalutamide, leuprolide, and goserelin, and immuno-modulating agents.

Therapeutic Compositions and Formulations

The subject invention further provides therapeutic compositions that contain a therapeutically effective amount of the therapeutic agent of the subject invention and a pharmaceutically acceptable carrier or adjuvant.

The therapeutic agent used in these therapies can be in a variety of forms. These include for example, solid, semi-solid, and liquid dosage forms, such as tablets, pills, powders, liquid solutions or suspensions, suppositories, and injectable and infusible solutions. The preferred form depends on the intended mode of administration and therapeutic application.

In a preferred embodiment, the composition is formulated in accordance with routine procedures as a pharmaceutical composition adapted for local injection administration to human beings. Typically, compositions for local injection administration are solutions in sterile isotonic aqueous buffer. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is administered by injection, an ampoule of sterile water for injection or saline can be provided so that the ingredients may be mixed prior to administration.

The subject invention also provides for a therapeutic method by administering therapeutic or pharmaceutical compositions in a form that can be combined with a pharmaceutically acceptable carrier. In this context, the compound may be, for example, isolated or substantially pure. The term "carrier" refers to a diluent, adjuvant, excipient, or vehicle with which the compound is administered. Such pharmaceutical carriers can be sterile liquids, such as water and oils, including those of petroleum oil such as mineral oil; vegetable oil such as peanut oil, soybean oil, and sesame oil; animal oil; or oil of synthetic origin.

Suitable carriers also include ethanol, dimethyl sulfoxide, glycerol, silica, alumina, starch, sorbitol, inosital, xylitol, D-xylose, manniol, powdered cellulose, microcrystalline cellulose, talc, colloidal silicon dioxide, calcium carbonate, magnesium cabonate, calcium phosphate, calcium aluminium silicate, aluminium hydroxide, sodium starch phosphate, lecithin, and equivalent carriers and diluents. Saline solutions and aqueous dextrose and glycerol solutions can also be employed as liquid carriers, particularly for injectable solutions.

Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The therapeutic composition, if desired, can also contain minor amounts of wetting or emulsifying agents, or pH buffering agents.

The amount of active ingredient that may be combined with the carrier materials to produce a single dosage form will vary, depending such as the type of the condition and the subject to be treated. The amount of active ingredient that may be combined with the carrier materials to produce a single dosage form will vary, depending such as the type of the condition and the subject to be treated. In general, a therapeutic composition contains from about 5% to about 95% active ingredient (w/w). More specifically, a therapeutic composition contains from about 20% (w/w) to about 80% or about 30% to about 70% active ingredient (w/w).

The therapeutic agent of the subject invention can be formulated according to known methods for preparing pharmaceutically useful compositions. Formulations are described in detail in a number of sources which are well known and readily available to those skilled in the art. For example, Remington's Pharmaceutical Science by E. W. Martin describes formulations which can be used in connection with the subject invention. In general, the compositions of the subject invention will be formulated such that an effective amount of the bioactive compound(s) is combined with a suitable carrier in order to facilitate effective administration of the composition.

The therapeutic or pharmaceutical compositions of the subject invention can also be formulated as neutral or salt forms. Pharmaceutically acceptable salts include those formed with free amino groups such as those derived from hydrochloric, phosphoric, acetic, oxalic, or tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

Routes of Administration

The compounds and compositions of the subject invention can be administered to the subject being treated by standard routes, including oral, or parenteral administration including intravenous, subcutaneous, topical, transdermal, intradermal, transmucosal, intraperitoneal, intramuscular, intracapsular, intraorbital, intracardiac, transtracheal, subcutaneous, subcuticular, intraarticular, subcapsular, subarachnoid, intraspinal, and epidural injection, infusion, and electroporation, as well as co-administration as a component of any medical device or object to be inserted (temporarily or permanently) into a subject.

The amount of the therapeutic or pharmaceutical composition of the subject invention effective in the treatment of breast cancer will depend on a variety of factors, such as the route of administration and the seriousness of the condition, and should be decided according to the judgment of the practitioner and each patient's circumstances. In general, the dosage ranges from about 0.01 µg/kg to about 10 mg/kg, about 0.01 µg/kg to about 1 mg/kg, about 0.01 µg/kg to about 100 µg/kg, about 0.01 µg/kg to about 10 µg/kg, or about 0.01 µg/kg to about 1 µg/kg. Such a unit dose may be administered once to several times (e.g. two, three and four times) every two weeks, every week, or every day.

In one embodiment, the compounds and compositions of the subject invention and any second therapeutic agent are administered simultaneously or sequentially to the patient, with the second therapeutic agent being administered before, after, or both before and after treatment with the compounds of the subject invention. Sequential administration may involve treatment with the second therapeutic agent on the same day (within 24 hours) of treatment with the subject compound. Sequential administration may also involve continued treatment with the second therapeutic agent on days that the subject compound is not administered.

In addition, in vitro assays may optionally be employed to help identify optimal dosage ranges. The precise dose to be employed in the formulation will also depend on the route of administration, and the seriousness of the disease, condition or disorder, and should be decided according to the judgment of the practitioner and each patient's circumstances. Effective doses may be extrapolated from dose-response curves derived from in vitro or animal model test systems.

Following are examples that illustrate procedures for practicing the invention. These examples should not be construed as limiting. All percentages are by weight and all solvent mixture proportions are by volume unless otherwise noted.

Example 1

Over-Expression of PCK-ι in Benign and Malignant Breast Biopsies

Figure 1:
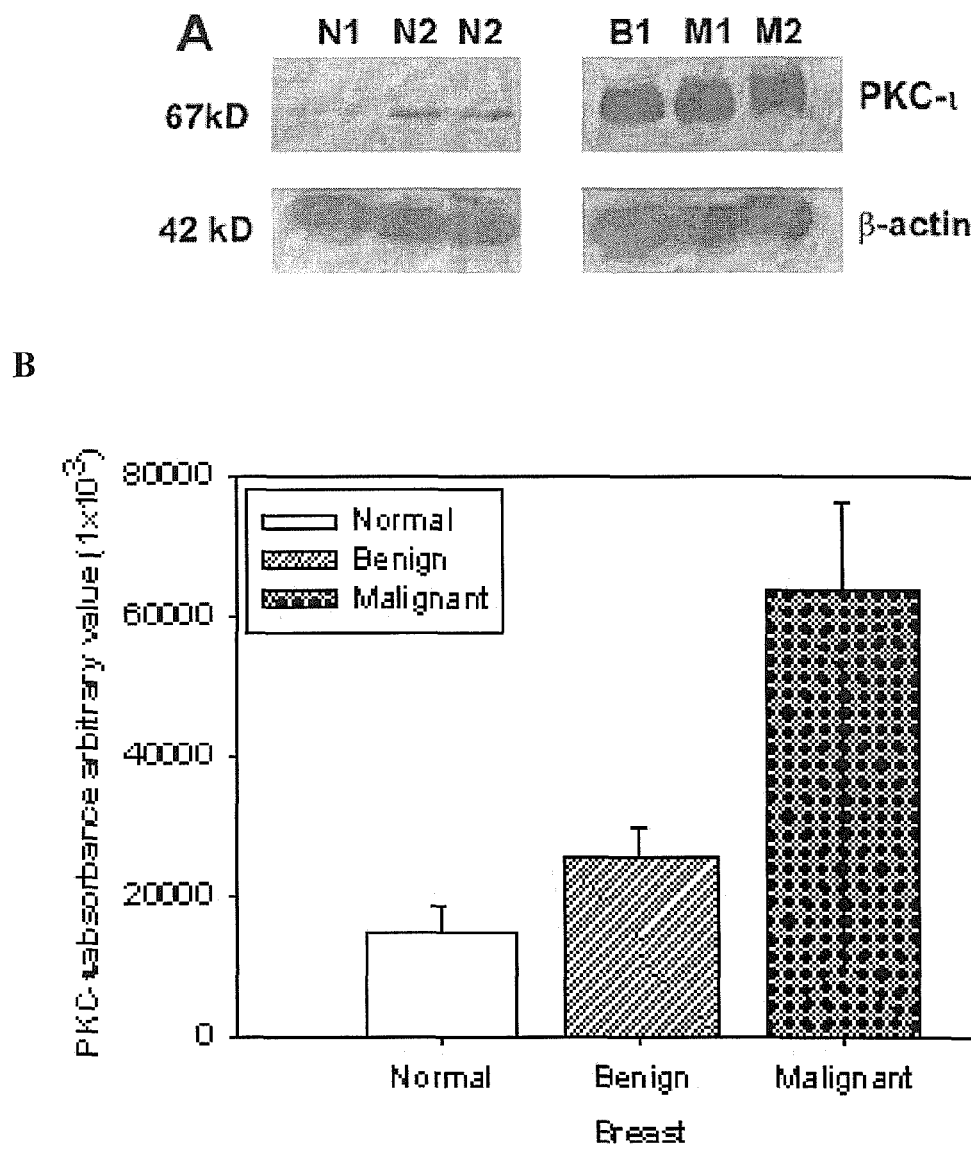
FIGS. 1A-B show that PKC-ι is over-expressed in benign and malignant breast biopsies. (A) Breast tissue biopsies (50 μg) were subjected to gel electrophoresis and Western blot analysis. Western blot was performed using monoclonal antibodies against PKC-ι (cat. #610176, BD Transduction, San Diego, Calif.) at a 1:2000 dilution (5 μg). Secondary antibodies obtained from Accurate JOM035146, Westbury, N.Y.) were used at a 1.5:10000 dilution (48 μg). To control equal loading of the proteins, β-actin was probed with goat polyclonal antibodies (SC-1616) at a 2.5:2000 dilution (10 μg) and secondary antibodies (SC-2350) at a 1:2000 dilution (8 μg, Santa Cruz Biotechnology). Du-145 cell lysates (50 μg) containing PKC-ι were used as positive control (not shown). (B) PKC-ι is over-expressed in malignant breast cancer tissue as compared to normal and benign breast tissue. Western blot results from 5 normal breast tissue specimens, 10 benign fibroadenoma tissue specimens and 11 malignant breast tissue specimens were quantified by densitometry. The mean plus and minus the standard error value is presented for each tissue type. Bars represent means with standard deviations.

This Example reveals that PKC-ι is present in high levels in benign and malignant breast tumor tissue, but is absent in normal breast tissue (FIG. 1). Briefly, breast tissue biopsy specimens were obtained from three normal subjects, a patient with fibroadenoma (benign), a patient with invasive ductual carcinoma, and a patient with invasive lobular carcinoma. 50 µg of each biopsy specimen was subjected to gel electrophoresis and Western blots with monoclonal antibodies against PKC-ι (cat. #610176, BD Transduction, San Diego, Calif.) at a 1:2000 dilution (5 µg). Secondary antibodies obtained from Accurate JOM035146, Westbury, N.Y.) were used at a 1.5:10000 dilution (48 µg). To control equal loading of the proteins, β-actin was also probed with goat polyclonal antibodies (SC-1616) at a 2.5:2000 dilution (10 µg) and secondary antibodies SC-2350 at a 1:2000 dilution (8 µg, Santa Cruz Biotechnology). Du-145 cell lysates (50 µg) containing PKC-ι were used as positive control for PKC-ι immuno-reactivity (not shown).

FIG. 1A shows that PKC-ι was abundantly present in fibroadenoma and invasive carcinoma tissue, but was absent in normal breast tissue. PKC-ι was identified by Western blots as a 67 kD band, which is consistent with the immuno-reactive signal obtained from Du-145 prostate cancer cells expressing PKC-ι (data not shown). Control β-actin Western blots showed β-actin immuno-reactive bands at a molecular weight of 42 kD. The β-actin immuno-reactive bands were of equal intensity, indicating that equal amount of protein was loaded into each lane. In addition, PKC-ι proteins detected with Western blots were quantified, and the mean plus and minus of the standard error (SE) value was calculated.

FIG. 1B shows Western blots probing for PKC-ι in normal breast tissue specimens (n=5), benign breast tissue specimens (n=9; i.e., fibroadenoma), and malignant breast tissue specimens (n=11; i.e., invasive and non-invasive ductal and lobular carcinoma). The results revealed that PKC-ι was present in low levels in normal and benign breast tissue (FIG. 1B). In comparison, there was a 435% increase in PKC-ι expression in malignant tissue as compared to normal tissue (P=0.008). Additionally, there was a 251% increase in PKC-ι expression in malignant tissue as compared to benign tissue (P=0.05). The levels of PKC-ι expression between normal and benign breast tissue were not significantly different. Control β-actin Western blots showed equal density of β-actin immuno-reactive bands at a molecular weight of 42 kD, indicating that equal amount of protein was loaded into each lane (Western blots not shown due to space limitations).

Example 2

Association of PCK-ι with the Proliferation and Survival of Breast Cancer Cells

Figure 2:
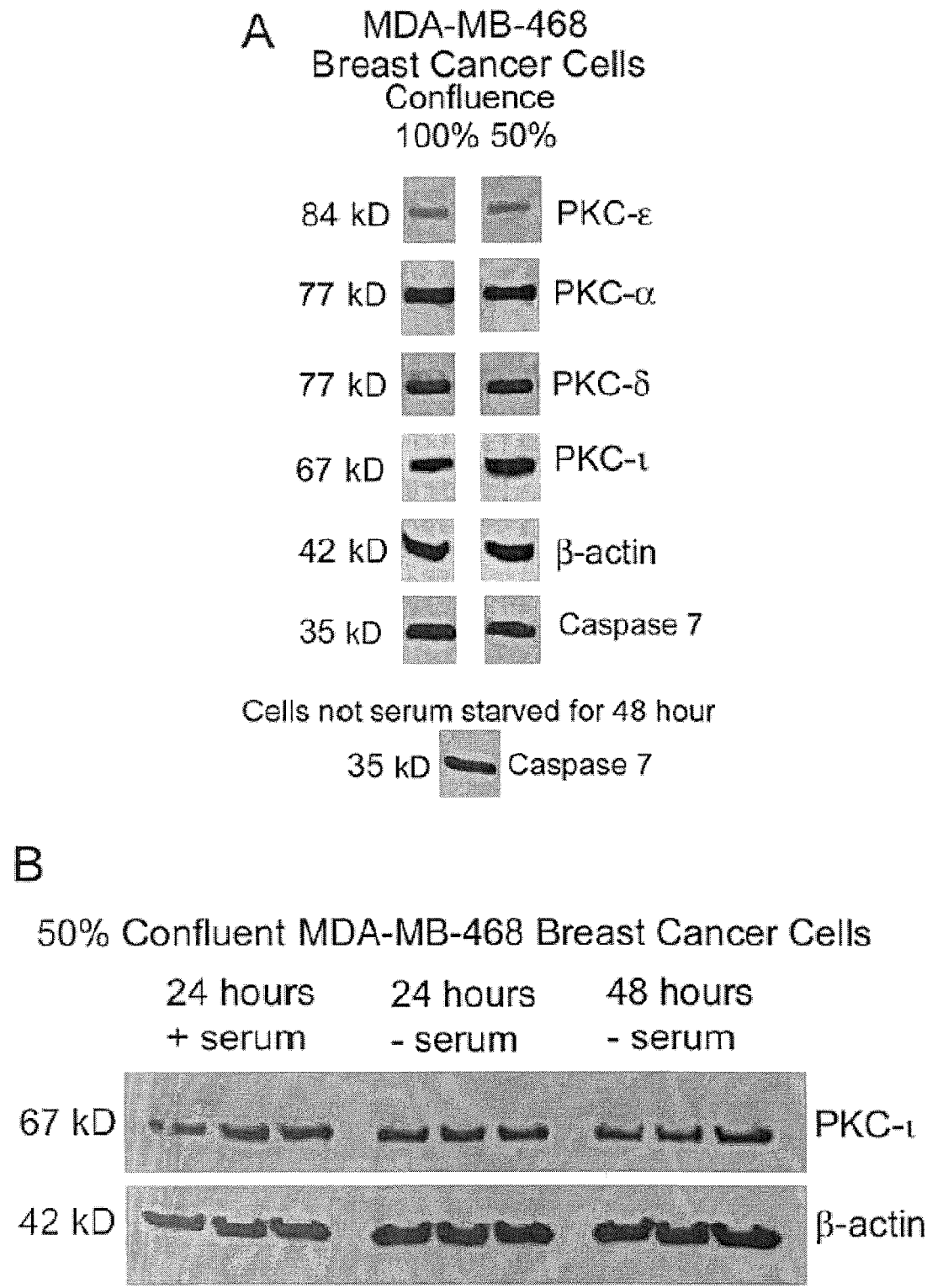
FIGS. 2A-B show the association of cell density with PKC-ι concentration in MDA-MB-468 breast cancer cells. (A) shows the expression of PKC isozymes in 100% and 50% confluent cells. 100% and 50% confluent cells were harvested at the indicated times and cell lysates were subjected to Western blot analysis. Equal amounts of cellular protein (15 μg) were loaded per well. (B) shows PKC-ι levels in 50% confluent cells cultured with or without serum. Independent triplicate total cell lysates from cells at 50% confluence were grown in the presence or absence of serum for 24 and 48 hours.

To investigate whether PKC-ι plays any role in the proliferation/survival of breast cancer cells, MDA-MB-468 human breast cancer cells were plated. Cell lysates were subject to Western blot analysis when cells reached 100% and 50% confluence. Western blot results showed that PKC-ι was present in large quantities in rapidly proliferating, 50% confluent cells (FIG. 2A). In comparison, PKC-ι protein content in 100% confluent cells was 43% lower than that in 50% confluent cells. Differences between PKC-ι protein content in 100% confluent and rapidly proliferating, 50% confluent cells were significant at P=0.04 (n=3).

To investigate whether PKC isozymes play any role in cell proliferation/survival, Western blots were performed to detect the levels of PKC-α, PKC-δ, and PKC-ε in 100% confluent and proliferating 50% confluent cells. Westerns blot results showed invariant levels of PKC-α, PKC-δ and PKC-ε in 100% confluent versus proliferating 50% confluent cells. The results showed that PKC-ι was up-regulated during the course of cell proliferation, while other PKCs such as PKC-α, PKC-δ and PKC-ε were not involved in the cell proliferation process.

FIG. 2B demonstrates that the significant increase in PKC-ι levels in 50% confluent serum-cultured cells is due to rapid cell proliferation, not serum stimulation. Specifically, 50% confluent cells were serum-starved for 24 hours, serum-starved for 48 hours, and serum-cultured for 24 hours, respectively, and the levels of PKC-ι were measured. The results showed that similar amounts of PKC-ι were present in serum-starved v. serum-cultured cells (FIG. 2B). Thus, the increase in PKC-ι in 50% confluent cells is not due to serum stimulation, but is due to the involvement of PKC-ι in cell proliferation/survival.

Example 3

PKC-ι as an Essential Factor for the Proliferation of Breast Cancer Cells

This Example reveals that PKC-ι is required for the proliferation and/or survival of breast cancer cells. Briefly, MDA-MB-468 breast cells were plated on 75 cm² flasks at a density of 3.75×10⁵ cells/flask. Twenty-four hours post plating, cells were incubated with either siRNA-A (120 nM; vehicle-control) or PKC-ι siRNA (120 nM) according to manufacture's instruction (Santa Cruz Biotechnology). During a 3-day incubation period, viable cells were counted by trypan blue dye exclusion assay. Cell viability and cell count were determined 24-72 hours following addition of either control short interfering RNAs (siRNA-A, vehicle control; 120 nM) or PKC-ι siRNA (120 nM) according to manufacturer's instruction (Santa Cruz Biotechnology).

Figure 3:
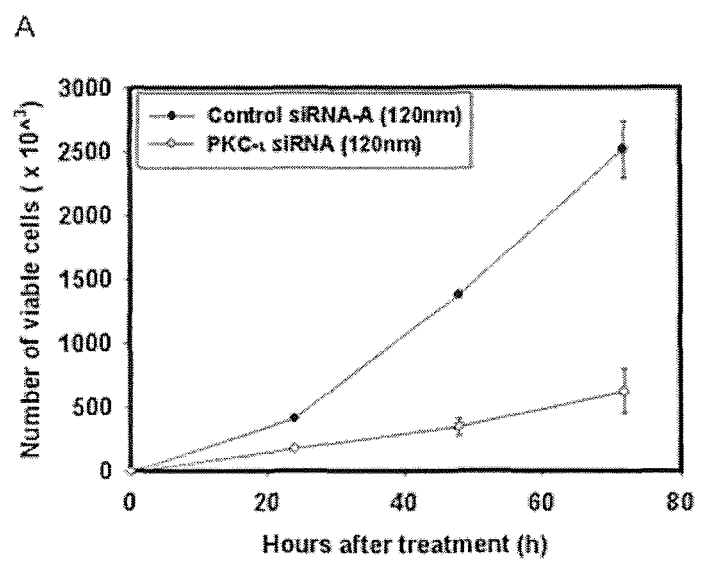
FIGS. 3A-C show the effects of PKC-ι siRNA on the proliferation of MDA-MB-468 breast cancer cells and PKC-ι protein content. (A) shows that PKC-ι siRNA significantly reduced the proliferation of breast cancer cells. Open symbols (O) represent control (siRNA-A) treated cells. Solid symbols (●) represent cells treated with PKC-ι siRNA. (B) shows Western blot results of PKC-ι protein content in cells treated with PKC-ι siRNA or control siRNA-A (upper panel). Control β-actin Western blots showed β-actin immuno-reactive bands at a molecular weight of 42 kD (lower panel). Band intensity was quantified by densitometry scanning. Molecular mass standard (kD) are shown on the left. Data is representative of two independent experiments. (C) shows bar graphs of PKC-ι protein content in cells treated with PKC-ι siRNA or control siRNA-A at 24 hr, 48 hr and 72 hr post-treatment.
Figure 3:
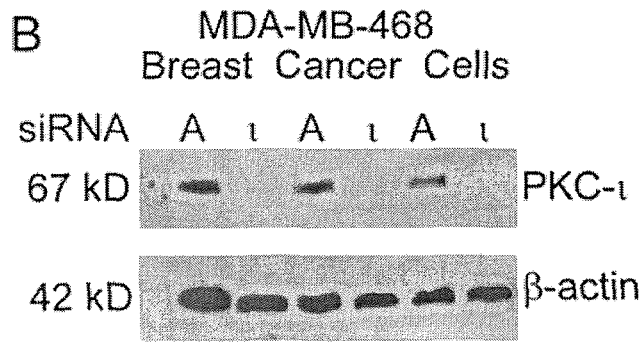
Figure 3:
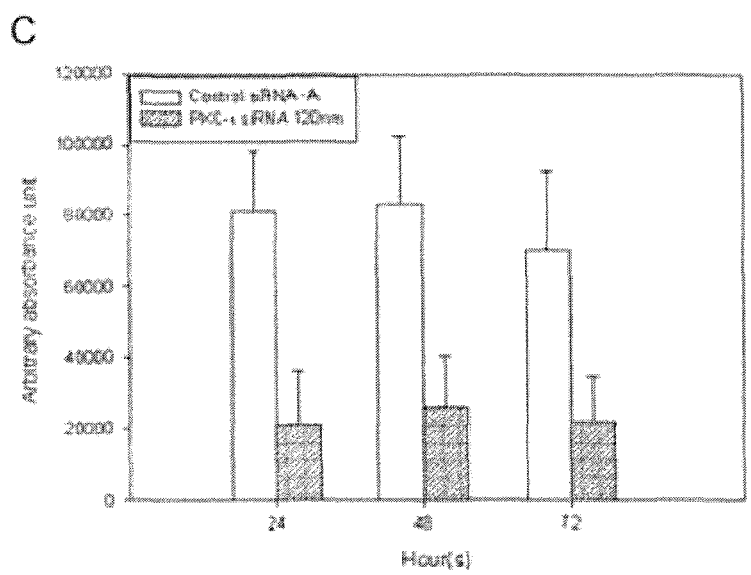

The results showed that exposure of MDA-MB-468 breast cancer cells to PKC-ι siRNA significantly reduced cell proliferation by 57% at 24 h (P=0.04), 75% at 48 h (P=0.04) and 75% at 72 h (P=0.02) post treatment (FIG. 3A). Densitometry scanning of Western blots revealed that exposure to PKC-ι siRNA decreased PKC-ι protein content by 74% (24 hours), 68% (48 hours), and 68% (72 hours) (FIGS. 3B and 3C; n=3 different experiments). Differences between PKC-ι protein content in control siRNA-A and PKC-ι siRNA treated cells were significant (P=0.002 at 24 hours; P=0.008 at 48 hours and P=0.036 at 72 hours) for all time points. Control β-actin Western blots showed β-actin immuno-reactive bands at a molecular weight of 42 kD. The β-actin immuno-reactive bands were of equal intensity, indicating that equal amounts of proteins were loaded into each lane. These results demonstrate that PKC-ι is required for cell proliferation/survival.

Example 4

Anti-Proliferative Effects of ICA-1 on Breast Cancer Cells

Figure 4:
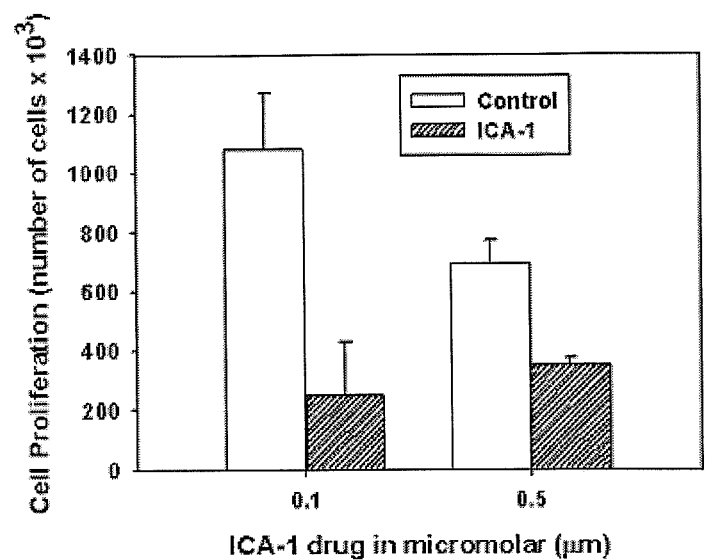
FIG. 4 shows the effects of the PKC-ι inhibitor ICA-1 on the proliferation of MDA-MB-468 breast cancer cells. Five thousand cells were plated in T-25 cm² flasks. Twenty-four hours post vehicle control or ICA-1 treatment, the number of viable cells was counted by Trypan blue exclusion. Data shown are the mean+/−SD of two independent experiments.

This Example demonstrates that ICA-1 inhibits the proliferation of breast cancer cells. Briefly, MDA-MB-468 breast cancer cells were treated with 0.1 µM or 0.5 µM ICA-1. Cell viability and cell count were determined 24 hours following addition of either vehicle control or ICA-1. As shown in FIG. 4, ICA-1 potently reduced the proliferation of MDA-MB-468 cells by 77% (0.1 µM) and 50% (0.5 µM; P=0.05). ICA-1 at 0.1 µM was more effective in inhibiting the proliferation of MDA-MB-468 cells than ICA-1 at 0.5 µM. This indicates that ICA-1 applied at 0.5 µM in vitro may induce multiple drug resistance (MDR).

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

We claim:

1. A method of treating breast cancer or tumor comprising administering, to a subject in need of such treatment, an effective amount of a PKC-iota inhibitor, and, optionally, a pharmaceutical acceptable carrier, wherein the PKC-iota inhibitor is 1H-imidazole-4-carboxamide,5-amino-1-[2,3-dihydroxy-4-[(phosphonoxy)methyl]cyclopentyl],[1R-(1α, 2β, 3β, 4α)] or a salt thereof.

2. The method according to claim 1, wherein the subject is a human.

3. The method of claim 1, wherein the subject has breast cancer.

4. The method of claim 3, wherein the subject has ductal carcinoma in-situ (DCIS), invasive ductal carcinoma (IDC), lobular carcinoma in-situ (LCIS), invasive lobular carcinoma (LCIS), medullary carcinoma, malignant phyllode tumor, tubular carcinoma, mucinous carcinoma, metastatic adenocarcinoma, or inflammatory breast cancer.

5. The method of claim 4, wherein the subject has invasive ductal carcinoma, invasive lobular carcinoma, or metastatic adenocarcinoma.

6. A method of inhibiting proliferation of breast cancer or tumor cells, comprising administering to the breast cancer or tumor cells an effective amount of a PKC-iota inhibitor, and optionally, a pharmaceutically acceptable carrier, wherein the PKC-iota inhibitor is 1H-imidazole-4-carboxamide,5-amino-1-[2,3-dihydroxy-4-[(phosphonoxy)methyl]cyclopentyl]-,[1R-(1α, 2β, 3β, 4α)] or a salt thereof.

7. The method of claim 6, wherein the breast cancer or tumor cells are of human origin.

8. The method of claim 7, wherein the breast cancer or tumor cells are selected from non-invasive ductal carcinoma cells, invasive ductal carcinoma cells, non-invasive lobular carcinoma cells, invasive lobular carcinoma cells, medullary carcinoma cells, malignant phyllode tumor cells, tubular carcinoma cells, mucinous carcinoma cells, metastatic adenocarcinoma cells, or inflammatory breast cancer cells.

* * * * *